United States Patent [19]

Chuang et al.

[11] Patent Number: 5,708,957
[45] Date of Patent: Jan. 13, 1998

[54] OPTICAL SENSOR WITH RADIOLUMINESCENT LIGHT SOURCE

[75] Inventors: Han Chuang; Mark A. Arnold, both of Iowa City, Iowa

[73] Assignee: University of Iowa Research Foundation, Iowa City, Iowa

[21] Appl. No.: 597,509

[22] Filed: Feb. 2, 1996

[51] Int. Cl.$^6$ .............................. G01N 21/64; C09K 11/04
[52] U.S. Cl. .................................. 422/82.07; 422/82.05; 422/82.08; 422/82.09; 436/127; 436/145; 436/163; 436/164; 436/172
[58] Field of Search ............................. 422/68.1, 82.05, 422/82.07, 82.08, 82.09, 82.11; 436/57, 164, 127, 68, 75, 145, 163, 166, 172, 800; 252/646, 301.4 P

[56] References Cited

U.S. PATENT DOCUMENTS

| | | | |
|---|---|---|---|
| 3,612,866 | 10/1971 | Stevens et al. | 250/71 |
| 4,810,655 | 3/1989 | Khalil et al. | 436/138 |
| 4,861,727 | 8/1989 | Hauenstein et al. | 436/136 |
| 4,889,660 | 12/1989 | Jensen et al. | 252/646 |
| 4,935,632 | 6/1990 | Hart | 250/486 |
| 4,997,597 | 3/1991 | Clough et al. | 252/646 |
| 5,100,587 | 3/1992 | Clough et al. | 252/646 |
| 5,151,603 | 9/1992 | Nakamura | 250/458.1 |
| 5,155,046 | 10/1992 | Hui et al. | 436/136 |
| 5,176,882 | 1/1993 | Gray et al. | 422/82.07 |
| 5,233,194 | 8/1993 | Mauze et al. | 250/341 |
| 5,272,088 | 12/1993 | Morlotti | 436/68 |
| 5,313,485 | 5/1994 | Hamil et al. | 372/69 |
| 5,496,997 | 3/1996 | Pope | 250/227.21 |
| 5,605,171 | 2/1997 | Tam | 136/253 |

OTHER PUBLICATIONS

*A Continuous, Implantable Lactate Sensor*; Baker, Gough; Anal. Chem, 1995, 67, 1536–1540.

*Luminescence Quenching Behavior of an Oxygen Sensor Based on a Ru(II) Complex Dissolved in Polystyrene*; Hartmann, Leiner, Lippitsch; Anal. Cheml 1995, 67, 88–93.

*Optical Fiber Sensor for Biological Oxygen Demand*; Preininger, Kilmani, Wolfbeis; Anal. Chem. 1994, 66, 1841–1846.

*Optical Triple Sensor for Measuring pH, Oxygen and Carbon Dioxide*; Weigl, Holobar, Trettnak, Klimant, Kraus, O'Leary, Wolfbeis, Journal of Biotechnology 32, (1994) 127–138.

*Solid State Radioluminescent Sources Using Tritium-Loaded Zeolites, and Their Proposed Use as Process Monitors*; Gill, Hawkins, Renschler; Fusion Technology, vol. 21, Mar. 1992.

*Photophysics and Photochemistry of Oxygen Sensors Based on Luminescent Transition-Metal Complexes*; Carraway, Demas, DeGraff, Bacon; Anal. Chem. vol. 63, No. 4, Feb. 15, 1991.

*Oxygen Optrode for Use in a Fiber-Optic Glucose Biosensor*; Moreno-Bondi, Wolfbeis, Leiner and Schaffar; ANal. Chem, 1990, 62, 2377–2380.

*Immobilized Transition-Metal Complex*; Bacon, Demas; Anal. Chem. 1987, 59, 2780–2785.

*Fiber Optical Fluorosensor for Determination of Halothane and/or Oxygen*; Wolfbeis Posch, Kroneis, Anal. Chem 1985, 57, 2558–2561.

*A Fast Responding Fluorescence Sensor for Oxygen*; Wolfbeis, Offenbacher, Kroncis, Marsoner, Mikrochimica Acta (Wein) 1984 I, 153–158.

Primary Examiner—Long V. Le
Attorney, Agent, or Firm—Woodard, Emhardt, Naughton Moriarty & McNett

[57] ABSTRACT

An optical sensor is disclosed which uses a radioluminescent light source to supply the incident radiation for detecting a selected substance in a test medium. The radioluminescent source includes a beta emitting radio isotope which energizes a co-immobilized luminophore to release light in a given wavelength for a chemical sensor operation. The radioluminescent source is coupled with a sensing matrix for detecting and quantifying the analyte of interest. The sensing matrix produces a characteristic signal based on either absorbance or fluorescence which varies according to the concentration of the selected analyte in the sample. A photodetector measures the resulting optical signal from which the analyte concentration is determined.

33 Claims, 5 Drawing Sheets

OPTICAL SENSOR WITH RADIOLUMINESCENT LIGHT SOURCE

BACKGROUND OF THE INVENTION

A. Field of the Invention

The present invention relates to sensors which produce an optical signal to indicate the presence and/or concentration of a specified substance.

B. Description of the Prior Art

Optical sensors have been used to detect and quantify the presence of a substance of interest in a test medium through fluorescence quenching. By this approach, a source of light is used to stimulate fluorescence of a flourophore compound. The presence and/or concentration level of the substance of interest can then be detected due to the quenching effect that the substance has on the intensity of the fluorescence.

Fluorescence quenching has been used, particularly, to detect and quantify oxygen ($O_2$) concentration. For such sensors, a ruthenium based compound or "ruthenium complex" has been used as the flourophore to provide the requisite fluorescence. The use of ruthenium complexes in oxygen sensors have been described in the following publications: Hartman, Leiner and Lippitsch, *Luminescence Quenching Behavior of an Oxygen Sensor Based on a Ru(II) Complex Dissolved in Polystyrene*, 67 ANAL. CHEM. 88 (1995); Carraway, Demas, DeGraff, and Bacon, *Photophysics and Photochemistry of Oxygen Sensors Based on Luminescent Transition-Metal Complexes*, 63 ANAL. CHEM. 337 (1991); and Bacon and Demas, *Determination of Oxygen Concentrations by Luminescence Quenching of a Polymer-Immobilized Transition-Metal Complex*, 59 ANAL. CHEM. 2780 (1987).

In addition to ruthenium complexes, other flourophores have also been used to detect oxygen, as described in the following publications: Wolfbeis, Posch and Kroneis, *Fiber Optical Fluorosensor for Determination of Halothan and/or Oxygen*, 57 ANAL. CHEM. 2556 (1985); and Wolfbeis, Offenbacher, Kroneis and Marsoner, *A Fast Responding Fluorescence Sensor for Oxygen*, I MIKROCHIMICA ACTA [WIEN] 153 (1984). U.S. Pat. Nos. 5,176,882 to Gray et al., 5,155,046 to Hui et al., and 4,861,727 to Hauenstein et al. also disclose various flourophores which may be used to detect oxygen. As shown in several of the above cited references, substances besides oxygen can also be detected through the use of a fluorescence quenching mechanism.

More generally, luminophores have been used to facilitate optical sensing. As used herein, a "luminophore" is a chemical species which reacts to the presence of a substance to produce an optical result. A flourophore is thus one type of luminophore. Another type of luminophore changes color in accordance with changes in the amount of a substance of interest. A sensor which utilizes this principle to detect pH and $Co_2$ is disclosed in Weigl, Holobar, Trettnak, Klimant, Kraus, O'Leary, and Wolfbeis, *Optical Triple Sensor for Measuring pH, Oxygen and Carbon Dioxide*, 32 JOURNAL OF BIOTECHNOLOGY 127 (1994).

Luminophore-based sensors typically use a LED or lamp as a light source, requiring an external power supply which can add noise and variability to sensor operation due to variations in the supply power. Where the power supply has a limited life, such as when batteries are used as the power source, the operation of the sensor is limited by the operational lifetime of the power supply. The need to provide a power supply can thus be a limiting factor for many remote sensing applications, such as for chemical sensing during space missions where power is scarce and long term stability is required.

SUMMARY OF THE INVENTION

As described herein, there is provided an optical sensor which is self-powered, and which is therefore particularly suited for many applications where the requirement for powering the sensing mechanism may be a limiting factor. In the following described preferred embodiment, an oxygen sensor is disclosed which is energized by a radioluminescent light source to detect a selected substance in a test medium. The sensor includes a luminophore matrix exposed to the test medium which absorbs light from the radioluminescent source. The sensing matrix produces an optical characteristic in response to the absorption of light from the radioluminescent source which varies with the presence of the selected substance. A photodetector detects the optical characteristic and provides a corresponding signal to indicate detection of the selected substance in the test medium.

By one aspect of the present invention, an optical sensor is provided with a continuous and reliable source of light from the energy released by the decay of a radioactive isotope in a radioluminescent material. The sensor is particularly useful in remote sensing systems, such as in deep sea or outer space applications. Also, such a sensor generally provides a more efficient and reliable optical sensing system for any application.

By another aspect of the present invention, an optical sensor is provided with a self-powered light source by the use of a radioluminescent material which includes a radioactive beta emitter constituent and a phosphor constituent energized by beta particles from the radioactive constituent to emit light. By appropriate selection of the phosphor compound, the wavelength of light produced by the radioluminescent source may be matched to a corresponding sensing matrix to optimally configure the sensor for the detection of a particular substance of interest.

As taught herein, an optical sensor is constructed which includes a sensing matrix that absorbs light from a radioluminascent source to produce an optical characteristic. The optical characteristic is detected by a photodedector which provides a corresponding signal. The optical characteristic and corresponding photodetector signal changes upon exposure of the sensing matrix to a selected substance. As used herein, "selected substance" means any type of chemical species, including, for example, $O_2$, $CO_2$, or pH level; and "optical characteristic" means any detectable property of the sensing matrix resulting from the absorption, reflection, or emission of electromagnetic radiation. Examples of optical characteristics include, but are not limited to, color, intensity of reflected or emitted light, and absorption or emission spectra.

Accordingly, one object of the present invention is to provide an optical sensor which has a self-powered light source.

Another object is to provide an optical sensing system with a self-powered light source having improved power efficiency, reliability, and long term operability.

Still another object of present invention is to provide an RL light source for a luminophore-based optical sensor which is optimally configured to detect a particular substance of interest.

Further objects, features, and advantages of the present invention shall become apparent from the detailed drawings and descriptions provided herein.

DESCRIPTION OF THE PREFERRED EMBODIMENTS

Figure 1:
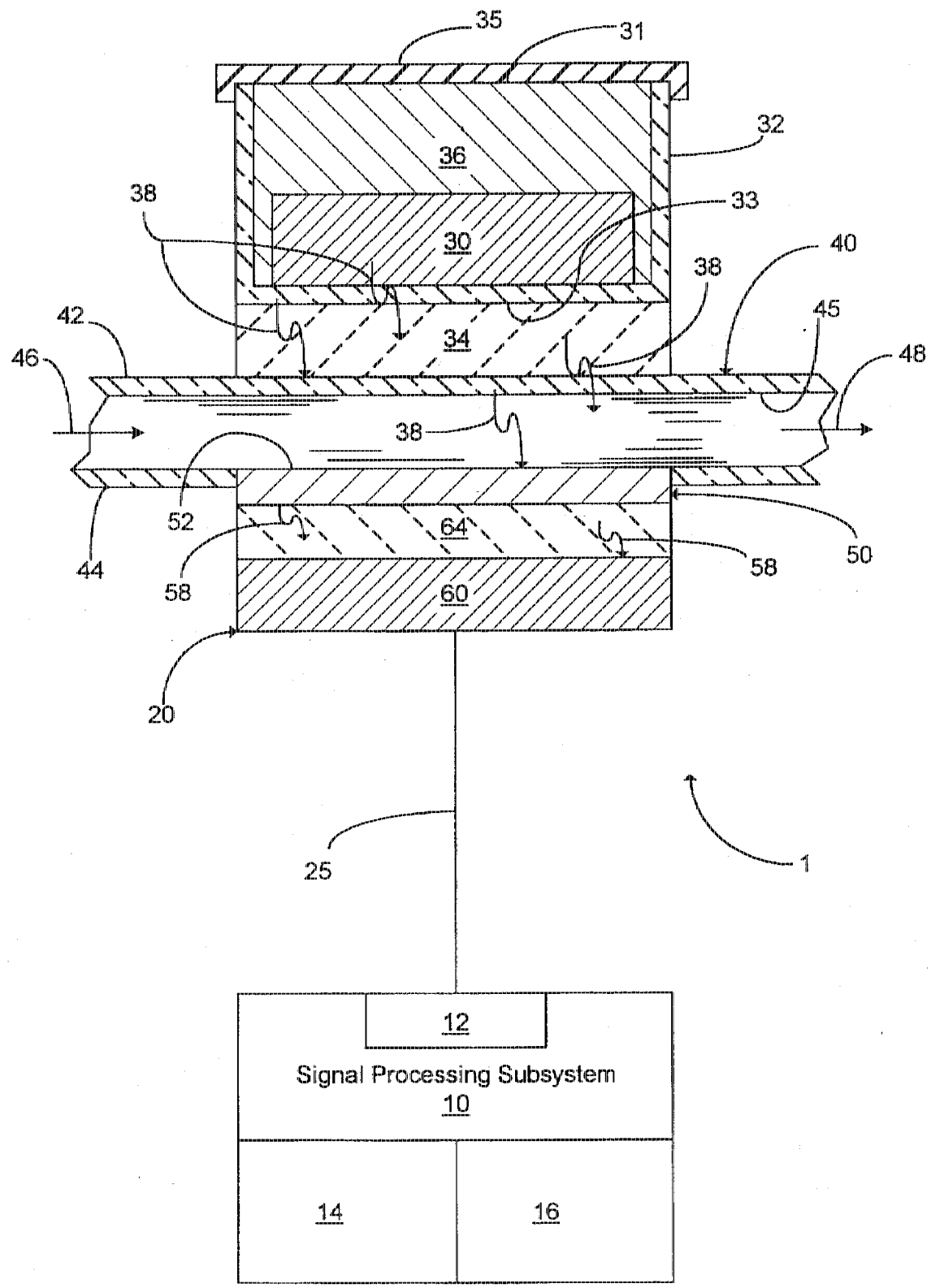
FIG. 1 is a schematic illustration of one preferred embodiment of an optical sensing system of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, any alterations and further modifications in the illustrated device, and any further applications of the principles of the invention as illustrated therein being contemplated as would normally occur to one skilled in the art to which the invention relates.

FIG. 1 schematically illustrates an optical sensor system 1 of the present invention. System 1 includes signal processing subsystem 10 coupled to sensor 20 by coupling 25. Sensor 20 is depicted in a schematic sectional view and includes a radioluminescent light (RL) source 30, test cell 40, sensing matrix 50, and photodetector 60. RL source 30 is enclosed or housed in container 32 along with plug 36. Container 32 has top portion 31 opposing transmission portion 33. Top portion 31 defines a closable opening (not shown) to facilitate placement of RL source 30 and plug 36 within container 32. Lid 35 provides for closure of container 32. Preferably, container 32 is manufactured from a transparent glass.

RL source 30 includes a radioactive isotope which supplies energy to produce light from radioactive decay. In one preferred embodiment, RL source 30 comprises a radioactive constituent which emits beta particles and a phosphor constituent which emits light in response to bombardment by beta particles from the radioactive constituent. The wavelength and intensity of light generated by this embodiment may be established by those skilled in the art by adjusting the type, amount, and relative orientation of the radioactive isotope and phophor constituents.

Light emitted by RL source 30 is symbolically represented by arrows 38. Plug 36 is configured to contain the beta radiation and provide mechanical strength to RL source 30. Plug 36 may be a conventional epoxy compound. Transmission portion 33 of container 32 is configured so that light from RL source 30 transmits therethrough. Optical filter 34 provides for the selective transmission of light from RL source 30 to test cell 40. As used herein, "optical filter" means any device which may be used to transmit a selected wavelength or selected range of wavelengths of electromagnetic radiation.

Test cell 40 includes opposing walls 42, 44 which define space 45 configured to receive a test medium. A test medium enters test cell 40 along a pathway indicated by arrow 46 and exits the pathway along arrow 48. Test cell wall 42 is configured to permit the transmission of light from optical filter 34 therethrough. Light also passes through space 45 containing the test medium before encountering sensing matrix 50. For this configuration, the test medium is a gas or liquid which permits the transmission of light therethrough. In other embodiments, the test cell may be configured to define a space configured to receive a test medium without walls or a particular pathway. For example, filter 34 and sensing matrix 50 may be positioned to define an appropriate test cell therebetween.

Sensing matrix 50 has sensing surface 52 adjacent space 45. Sensing matrix 50 is stimulated by the absorption of light transmitted from RL source 30. Preferably, sensing matrix 50 is permeable to facilitate detection of a desired substance in a test medium contained within test cell 40 via sensing surface 52. In one preferred embodiment, sensing matrix 50 is configured to immobilize a luminophore compound within a membrane or film which is permeable to the substance of interest. This configuration reduces abrasion and leaching of the luminophore compared to direct exposure on sensing surface 52 exposed to the test medium. However, in other embodiments, the sensing matrix may include a luminophore on a surface and the sensing matrix configuration may be other than a membrane or film.

Sensing matrix 50 produces an optical characteristic which varies with the presence of a selected substance in test cell 50. This varying optical characteristic is represented by arrows 58 and is detected by photodetector 60 through optical filter 64. For one embodiment, this optical characteristic is the intensity of light detected by photodetector 60 as a function of sensing matrix color. For another embodiment, this optical characteristic includes fluorescence intensity of the sensing matrix.

Photodetector 60 provides a signal corresponding to the optical characteristic which is input to signal processing subsystem 10 via coupling 25. Subsystem 10 is schematically depicted and processes the input sensor signal to provide sensing information using conventional techniques. Subsystem 10 includes signal conditioning portion 12 which may provide signal filtering, amplication, linearization, and other conventional signal conditioning. Subsystem 10 also includes display 14 to provide sensing information to an operator. A recording device 16 is also shown which may be used to record sensing information derived from the photodetector signal. This record may include the photodetector signal relative to another parameter such as time or test medium flow rate through test cell 40.

Photodetector 60 may be a photomultiplier tube or photodiode of a conventional type electrically connected to subsystem 10 by coupling 25. Coupling 25 schematically corresponds to the type of photodetector 10 selected and typically will include multiple electrical interconnections. Subsystem 10 may be configured for electronic, electrical, mechanical, and electromechanical devices of a conventional type which are interconnected to meet sensor detection and analysis requirements. Preferably, subsystem 10 is a programmable microprocessor-based system and signal conditioning portion 12 includes appropriate analog to digital conversion circuitry. In one embodiment, subsystem 10 includes a calibration means (not shown). Preferably, subsystem 10 may be adapted for use with multiple sensors.

One configuration of the preferred embodiment of sensing system 1 is next discussed which is particularly designed to detect oxygen. For this configuration, RL source 30 of sensor 20 includes $^{147}$Pm as the radioactive constituent and ZnS:Ag as the phosphor constituent. Beta particles from the radioactive decay of the $^{147}$Pm isotope energize the ZnS:Ag phosphor to produce blue light. This light is transmitted through transmission portion 33, optical filter 34, wall 42, and space 45 to sensing matrix 50.

Sensing matrix 50 has a flourophore portion that emits fluorescent light in response to the absorption of blue light from RL source 30. This flourophore is the ruthenium complex tris(4,7-diphenyl-1,10-phenanthroline) ruthenium (II) chloride (Ru(dpp)$_3$). Preferably, sensing matrix 50 for this embodiment further includes an oxygen permeable Polyvinyl Chloride (PVC) membrane in which the ruthenium complex is immobilized. Flourescence from the flourophore portion is quenched by $O_2$. When a test medium with $O_2$ passes through test cell 40 along arrows 46, 48, the intensity of the fluorescence emitted by sensing matrix 50 decreases with increasing $O_2$ concentration. The intensity of the fluorescence emission provides an optical characteristic indicative of $O_2$ concentration which is detected by photodetector 60. Photodetector 60 inputs a corresponding signal to subsystem 10. Subsystem 10 conditions the signal and provides a display and record of information corresponding to the signal. For this configuration, optical filters 34 and 64 are used to improve linearity of the sensor by reducing stray radiation. Filter 34 selectively passes light to excite the fluorophor while filter 64 passes only the light emitted from the excited fluophore.

Figure 2:
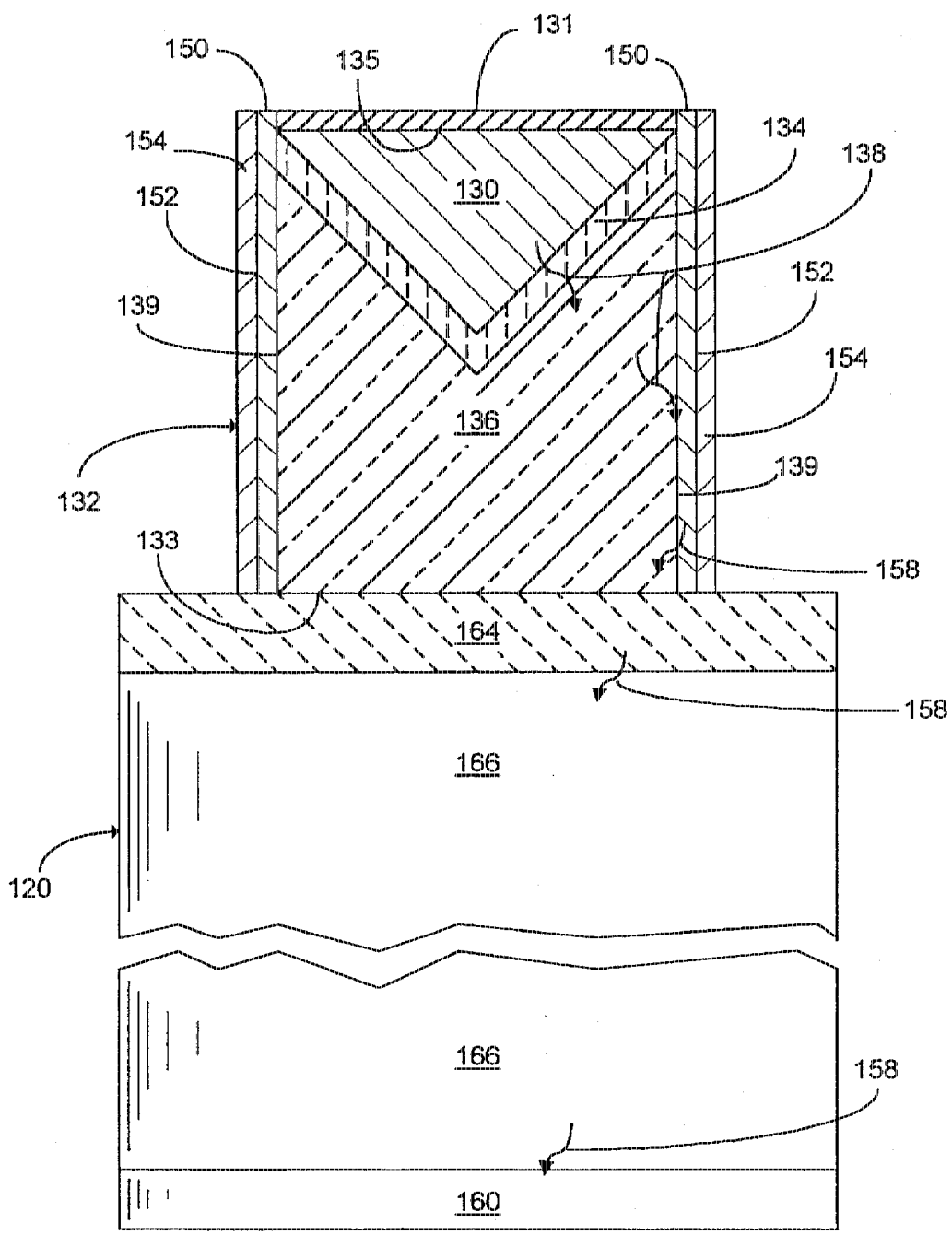
FIG. 2 is a schematic illustration of one preferred embodiment of a probe sensor of the present invention.

FIG. 2 shows sensor 120 of the present invention depicted in a partial schematic sectional view. Sensor 120 includes RL source 130 housed within probe 132. Probe 132 has generally cylindrical probe body 136 with tip 131 opposing base 133. Preferably probe body 136 is formed from transparent glass. RL source 130 is optically coupled to probe body 136 via optical filter 134. Mirror 135 is positioned at tip 131 of probe 132 to reflect light from RL source 130 into probe body 136.

RL source 130 emits light into probe body 136 as represented by arrows 138. At least a portion of this light is absorbed by sensing matrix 150 configured as a cylindrical membrane coupled to outer surface 139 of probe 132. Sensing surface 152 of sensing matrix 150 is at least partially covered by coating 154 to block ambient light. Other embodiments may not include coating 154. In one embodiment, coating 154 is an opaque silicone compound.

Probe 132 is configured for exposure to a test medium including the substance or substances to be detected by sensor 120. Notably, the test medium need not transmit light to sensing matrix 150. Sensing matrix 150 responds to the presence of the selected substance to provide a detectable optical characteristic. Arrows 158 represent this optical characteristic. This optical characteristic is detected by photodetector 160. Optical filter 164 and optical fiber 166 are coupled to sensing matrix 150 and photodetector 160 to transmit the optical characteristic from probe 132 to photodetector 160. Photodetector 160 provides a signal corresponding to the optical characteristic. A signal processing subsystem (not shown) similar to subsystem 10 shown in FIG. 1 may be used to process a signal from photodetector 160 via appropriate electrical coupling.

Sensor 120 may be configured to detect oxygen using an RL source 130 that includes $^{147}$Pm and phosphor ZnS:Ag to generate blue light. This light may be used to excite a ruthenium complex flourophore contained in sensing matrix 150. Fluorescent intensity indicative of oxygen quenching may be detected by photodetector 160 via optical filter 164 and optical fiber 166. Optical fiber 166 is depicted with a break to schematically represent the relative greater length of optical fiber 166 compound to probe 132 in typical applications.

Sensing matrix 150 and coating 154 are configured to permit the passage of the substance being detected to the flourophore portion of the sensor. Coating 154 is preferably opaque to reduce the amount of ambient light reaching the sensing matrix through the test medium and thereby improve noise immunity of system 101. Optical filters 134 and 164 are used to improve sensor 120 linearity and reduce optical noise from background radiation.

Referring generally to FIGS. 1 & 2, photodetector 60, 160 may be a photomultiplier tube, photodiode, or other type of photodetection device as would occur to those skilled in the art. In other embodiments, fewer or more optical filters 34, 64, 134, 164 could be used as would occur to those skilled in the art. Generally, the optical filter is matched to the detected optical characteristic of the sensing matrix 50, 150 and light spectrum emitted by RL source 30, 130. The solid diagonal lines used to portray items 30, 36, 50, 60, 130, 150, and 154 are not intended to indicate a specific type of material, but rather generally depict a cross-sectional view.

Besides a sensing matrix with Ru(dpp)$_3$ in PVC, tris(1,10-phenanthroline) ruthenium (II) chloride (Ru(phen)$_3$) immobilized in a silicone substance also provides a sensing matrix suitable to detect oxygen when energized by an RL source. Other ruthenium complexes may also be used. For example, ruthenium complex matrices including, but not limited to: (1)Ru(dpp)$_3$ in polystyrene, Ru(dpp)$_3$ in sol-gel, and ruthenium-tris (dipyridyl)-dichloride in silicone may be used as suitable fluorophores. In addition, polycyclic aromatic hydrocarbons (PAHs) in a glass support and PAHs in a polymer may be used in a fluorescence quenching type oxygen sensor powered by an RL source. The previously cited publications mention other compounds as well which could also be used as a fluorophore to be stimulated by light from an RL source in an optical sensor. Generally, these flourophores may be used in accordance with the present invention with conventional modifications to optical filters and phosphors as are known to those skilled in the art.

It is to be appreciated that in accordance with the present invention, a variety of biosensors can be constructed to monitor biochemical reactions. Such a biosensor may be made, for example, by coupling an oxygen sensor of the present invention to an appropriate oxydase enzyme or yeast. Such biosensors could be used to sense a wide variety of biological substances and reactions, including cholesterol, glutamate, glucose, lactate, and biological oxygen demand. Biosensing techniques which could incorporate a sensing mechanism of the present invention are described in the following publications: Baker and Gough, *A Continuous, Implantable Lactate Sensor*, 67 ANAL. CHEM. 1536-52 (1995); Li and Walt, 67 ANAL. CHEM. 3746-52 (1995); Preininger, Klimant and Wolfbeis, *Optical Fiber Sensor for Biological Oxygen Demand*, 66 ANAL. CHEM. 1841-46 (1994); and Moreno-Bondi, Wolfbeis, Leiner and Schaffar, *Oxygen Optrode for Use in a Fiber-Optic Glucose Biosensor*, 62 ANAL. CHEM. 2377-80 (1990).

Also, it is to be appreciated that optical sensors of the present invention can be constructed to detect a variety of substances in addition to oxygen. For one embodiment, an optical sensor useful to detect $CO_2$ may be energized by light from an RL source. The sensing matrix for this sensor includes a luminophore portion which displays a change in color based on the concentration of $CO_2$. As a result, a variable absorption of light form the RL source provides a variable light intensity level suitable for detection by a photodetector. Similarly, a sensor to detect solution pH may be constructed using a properly selected RL source and sensing matrix configured with a luminophore portion. Table 1 provides a listing of examples of matching constituents of RL light sources, luminophores, and preferred matrix fillers for $O_2$, $CO_2$, and pH sensing mechanisms.

TABLE 1

| Sensor | RL source | Luminophore | Filler |
|---|---|---|---|
| $O_2$ | ZnS:Ag and $^{147}$Pm | ruthenium complexes | silicon/PVC/ polystyrene |
| $CO_2$ | $Y_3(Al, Ga)_5O_{12}$:Ce and $^{147}$Pm | m-cresol purple | ethyl cellulose |
| pH | $Y_2O_2S$:Eu and $^{147}$Pm | Merck N9 | cellulose triacetate |

Besides $^{147}$Pm, other radioactive isotopes may be selected which are suitable for the RL source including $^3$H and $^{14}$C. In addition, the previously cited publications provide further examples of luminophore-based optical sensors which may be adapted for use with a self-powered light source in accordance with the present invention.

EXPERIMENTAL SECTION

The following examples are provided to further describe the objects, features, and advantages of the present invention, the same is to be considered as illustrative and not restrictive or limiting in character.

Example 1

In one experiment, a self-powered optical sensor was constructed in accordance with the present invention using an RL source. The RL source included 20 uCi of $^{14}$C as the radioactive isotope in a $^{14}$C-hexadecane radioactive constituent. The phosphor constituent of the RL source included 0.05 gram of ZnS:Ag. The RL source provided a source of blue light. The luminophore was a ruthenium complex of tris(1,10-phenanthroline) ruthenium (II) chloride (Ru(phen)$_3$). The Ru(phen)$_3$ flourophore was immobilized in a silicone compound in the form of a membrane to provide the sensing matrix.

The sensor was constructed by enclosing the RL source in the bottom of a glass vial and fixing an epoxy plug over it. A plastic lid was used to seal the top of the vial. The sensing membrane was attached to the bottom of the glass vial adjacent a space configured for a flow through sample. The sensing membrane and container were spaced apart from the surface of a photomultiplier tube to define the sample space. Distinct signal changes were observed when the sample space was alternatively filled with pure nitrogen and oxygen.

Example 2

In another experiment, the RL source was constructed in the following manner. In a 3.4×0.7 cm outer diameter glass vial, 15.2 milligrams of the phosphor constituent ZnS:Ag was completely mixed with 110.3 microliters of 1 molar NaOH, then 94.3 microliters of $^{147}$PMCl$_3$ solution (activity= 0.5 mCi) was added to serve as the radioactive constituent. After the vial was air-dried in a fume hood for 4 days, the dry residue was covered by 0.8 milliliters of epoxy (epo-tek 301, Epoxy Technology Inc.) and oven-cured for 1 hour at 65° C. The vial was then covered with a plastic lid, sealed with a thick layer of epoxy, and oven-cured for 1 hour at 65° C. The glow from the radioactive ZNS:Ag layer was visible to the eye in darkness. Tris(4,7-diphenyl-1,10-phenanthroline) ruthenium (II) chloride (Ru(dpp)$_3$) was immobilized in a layer of PVC. The resulting membrane was dip-coated on the outer surface of the vial to provide a sensing matrix. The components of the polymer solution for preparing the PVC membrane were 10 milliliters tetrahydrofuran (THF), 1.5 milliliters methanol, 1 gram PVC, 40.5 milligrams Ru(dpp)$_3$ and 5 milliliters 2-nitrophenyl octyl ether.

Figure 3:
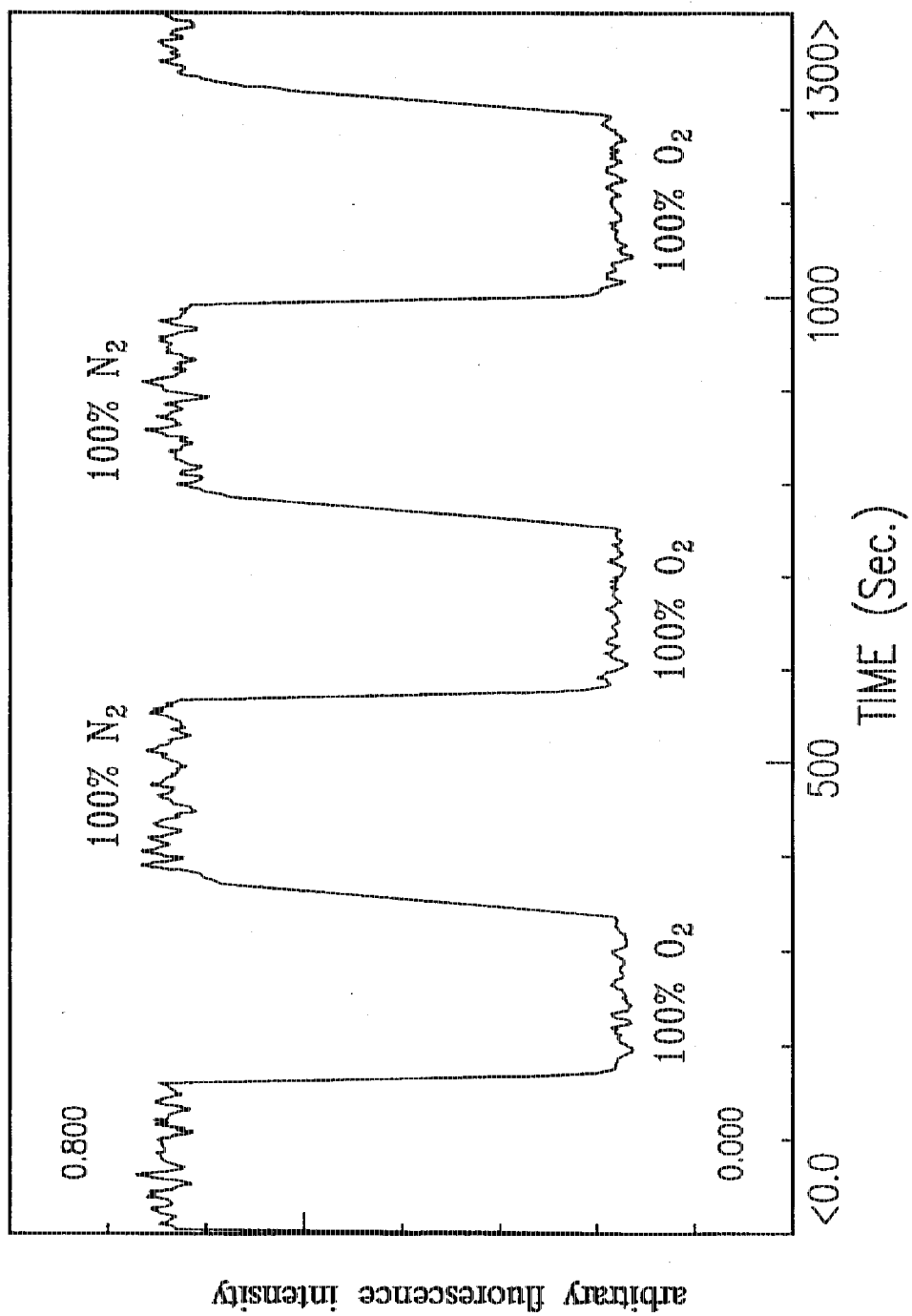
FIG. 3 is an intensity-time profile for one preferred embodiment of an oxygen sensor of the present invention.

FIG. 3 shows the response of the oxygen sensor to alternating nitrogen and oxygen exposure using the detection optics of a SLM AMINCO SPF-500C spectrofluorometer to monitor the Ru(dpp)$_3$ fluorescence. A calibration curve for this novel oxygen sensor is shown as a conventional Stern-Volmer plot in FIG. 4. Important sensor characteristics are:

1. Detection limit: 3.4 torr (0.45%) $O_2$;
2. Dynamic range: 3.4–760 torr; and
3. 95% response time: 12.5 ± 0.6 seconds.

Figure 4:
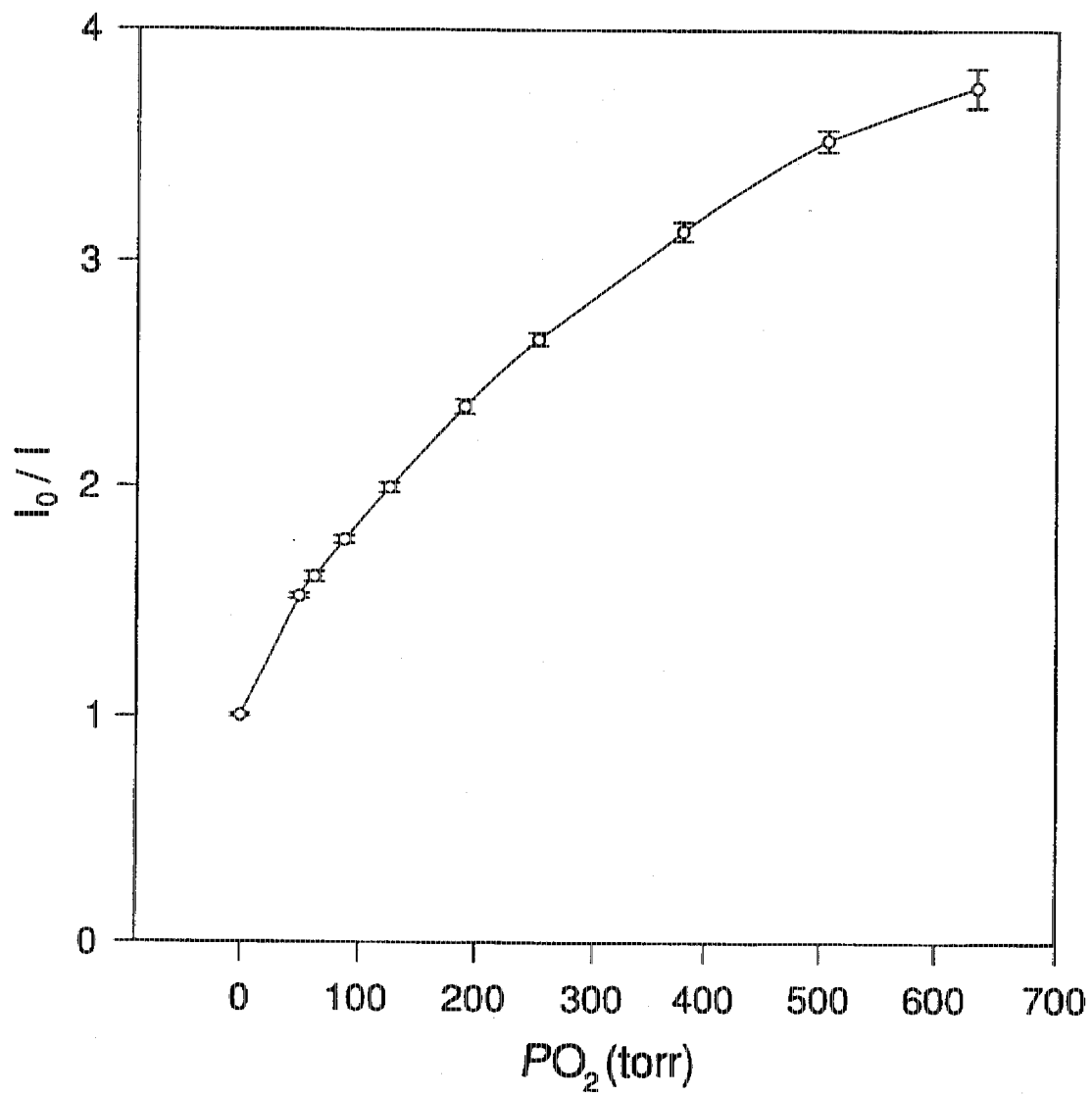
FIG. 4 is a calibration curve for the oxygen sensor profiled in FIG. 3.
Figure 5:
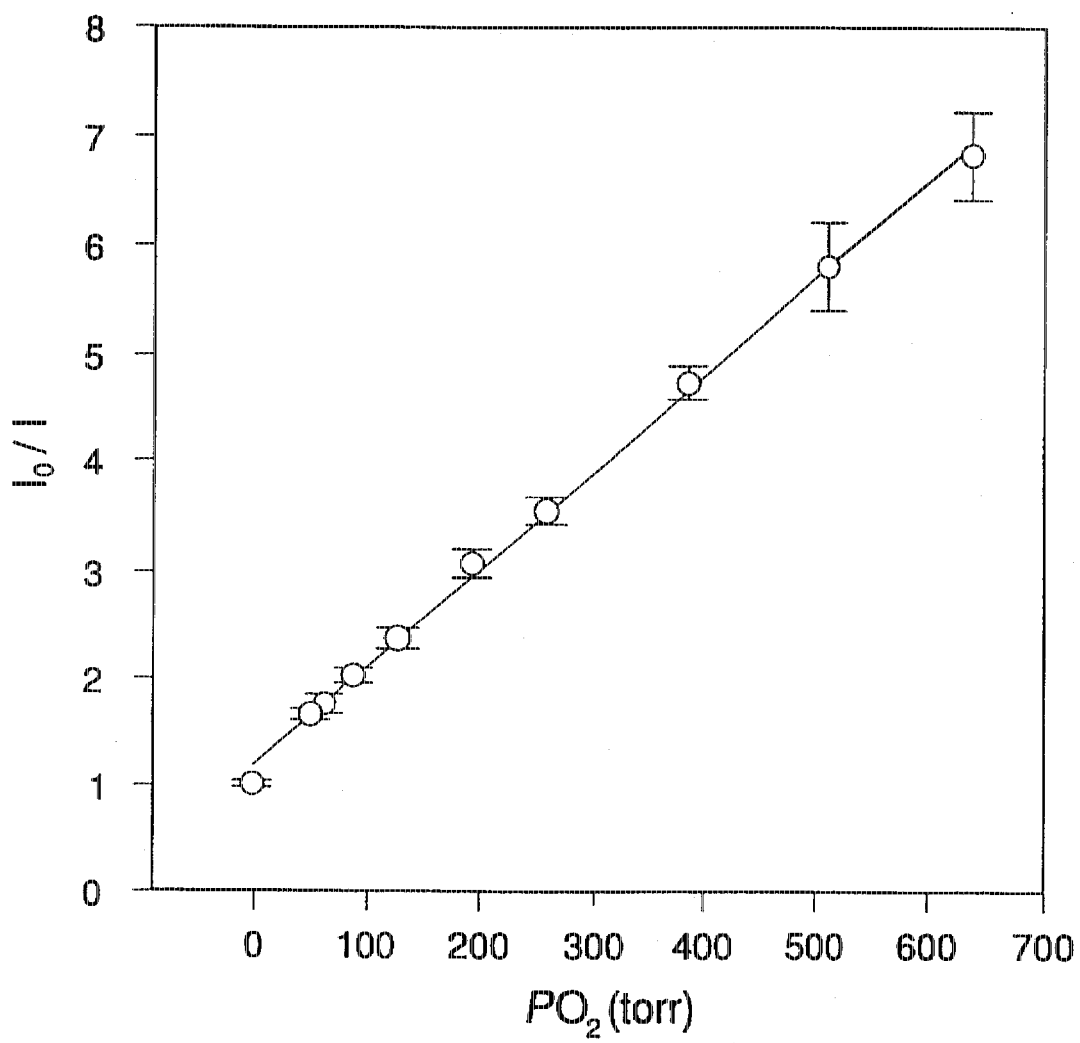
FIG. 5 is a calibration curve for the oxygen sensor profiled in FIG. 3 with improved linearity.

The downward curvature of the calibration curve in FIG. 4 was improved by placing a blue optical filter between the RL source and the sensing matrix. FIG. 5 depicts the improved calibration curve as a comparison with FIG. 4 demonstrates.

All publications, patents, and patent applications cited in this specification are herein incorporated by reference as if each individual publication, patent, or patent application were specifically and individually indicated to be incorporated by reference.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An optical sensor for detecting a selected substance, comprising:
    a radioluminescent light source, including:
        a radioactive constituent,
        a phosphor constituent energized by radiation from said radioactive constituent to emit light;
    a sensing matrix absorbing light from said radioluminescent light source to produce an optical characteristic, the optical characteristic changing upon exposure of said sensing matrix to the selected substance; and
    a photodetector configured to detect the optical characteristic and provide a corresponding signal to indicate detection of the selected substance.

2. The optical sensor of claim 1, wherein:
    said radioactive constituent includes a beta particle emitter; and
    said sensing matrix has a luminophore portion.

3. The optical sensor of claim 2, wherein the selected substance includes $O_2$, said phosphor constituent includes ZnS:Ag, said luminophore portion includes a ruthenium complex fluorophore, and the optical characteristic includes fluorescence.

4. The optical sensor of claim 2, wherein the selected substance is pH of a solution, said phosphor constituent includes $Y_2O_2S$:Eu, said luminophore portion includes Merck N9, and the optical characteristic includes color of said sensing matrix.

5. The optical sensor of claim 2, wherein the selected substance is $CO_2$, said phosphor constituent includes $Y_3(Al, Ga)_5O_{12}$:Ce, said luminophore portion includes m-cresol purple, and the optical characteristic includes color of said sensing matrix.

6. The optical sensor of claim 1, wherein said sensing matrix has a luminophore portion and said luminophore portion includes a compound selected from the group consisting of:

Ru(dpp)$_3$;
Ru(phen)$_3$;
Merck N9; and
m-cresol purple.

7. The optical sensor of claim 1, wherein said radioactive constituent includes one of $^3$H, $^{14}$C, and $^{147}$Pm and said phosphor constituent includes one of Y$_2$O$_2$S:Eu, Y$_3$(Al,Ga)$_5$O$_{12}$:Ce, and ZnS:Ag.

8. An optical sensing system for detecting concentration of a selected substance in a test medium, comprising:
 a radioluminescent source emitting light;
 a sensing matrix exposed to the test medium, said sensing matrix absorbing light from said radioluminescent source to produce an optical characteristic, the optical characteristic varying in accordance with concentration of the selected substance in the test medium; and
 a photodetector configured to detect the optical characteristic and provide a corresponding signal to indicate concentration of the selected substance in the test medium.

9. The optical sensing system of claim 8, wherein said radioluminescent source includes:
 a radioactive material emitting beta particles; and
 a phosphor material energized by beta particles from said radioactive material to emit light.

10. The optical sensing system of claim 8, wherein said photodetector includes a photodiode.

11. The optical sensing system of claim 8, wherein said photodetector includes a photomultiplier tube.

12. The optical sensing system of claim 8, further comprising an optical filter positioned between said sensing matrix and one of said radioluminescent source and said photodetector.

13. The optical sensing system of claim 8, further comprising a container enclosing said radioluminescent source, said container being positioned to define a test cell between said sensing matrix and said radioluminescent source, and said test cell being configured to receive the test medium.

14. The optical sensing system of claim 13, wherein said photodetector includes a photodiode, said sensing matrix includes a membrane coupled to the photodetector, said membrane has a surface exposed to the test medium, and further comprising:
 a first light filter positioned between said container and said test cell;
 a second light filter positioned between said membrane and said photodetector; and
 a signal processing subsystem electrically coupled to said photodetector, said signal processing subsystem including a display for providing a indication of the substance concentration to an operator.

15. The optical sensing system of claim 8, further comprising:
 a probe housing said radioluminescent source, said probe having:
  an outer surface coupled to said sensing matrix, said sensing matrix having a sensing surface configured to contact said test medium,
  a mirror adjacent said radioluminescent source to reflect electromagnetic radiation emitted therefrom,
  a body configured to transmit light from said radioluminescent source to said sensing matrix;
 an optical fiber coupling said probe to said photodetector, said optical fiber and said probe being configured to transmit electromagnetic radiation from said sensing matrix to said photodetector;
 an optical filter positioned between said photodetector and said radioluminescent source; and
 a coating covering at least a portion of said sensing surface to prevent intrusion of ambient light.

16. An optical sensor for detecting a selected substance in a test medium, comprising:
 a radioluminescent source emitting light;
 a sensing matrix having a fluorophore portion, said sensing matrix being exposed to the test medium, said sensing matrix providing a fluorescent emission in response to absorption of light from said radioluminescent source; and
 a photodetector detecting a first intensity of the fluorescent emission when the test medium does not include the selected substance and said photodetector detecting a second intensity of the fluorescent emission when the test medium includes the selected substance, said second intensity differing from said first intensity.

17. The optical sensor of claim 16, wherein said fluorophore portion includes a ruthenium complex.

18. The optical sensor of claim 16, wherein said fluorophore portion includes a PAH compound.

19. The optical sensor of claim 16, wherein said sensing matrix includes one of:
 Ru(dpp)$_3$ in a polystyrene membrane;
 Ru(dpp)$_3$ in a sol-gel membrane; and
 Ru(phen)$_3$ in a silicone membrane.

20. The optical sensor of claim 16, wherein said radioluminescent source includes:
 a radioactive constituent emitting beta particles; and
 a phosphor constituent emitting light in response to beta particles from said radioactive constituent.

21. The sensor of claim 16, further comprising:
 a container for enclosing said radioluminescent source and being configured to transmit light from said radioluminescent source to said sensing matrix; and
 a coupling means for positioning said sensing matrix relative to said container, said photodetector, and the test medium.

22. The optical sensor of claim 1, wherein said sensing matrix is spaced apart from said radioluminescent light source to define a test cell therebetween.

23. The optical sensor of claim 8, wherein said sensing matrix includes a film containing a fluorophore configured to detect oxygen, and said film is spatially separated from said radioluminescent light source.

24. The optical sensor of claim 16, wherein said sensing matrix includes a film with said fluorophore portion, and said film is spatially separated from said radioluminescent light source.

25. An optical sensing system for detecting a selected substance, comprising:
 a radioluminescent light source, including:
  a radioactive constituent,
  a phosphor constituent energized by radiation from said radioactive constituent to emit light;
 a sensing matrix absorbing light from said radioluminescent light source, said sensing matrix being defined separately from said radioluminescent light source to produce an optical characteristic, said optical characteristic changing upon exposure of said sensing matrix to the selected substance; and
 a photodetector configured to detect the optical characteristic and provide a corresponding signal to indicate detection of the selected substance.

26. The system of claim 25, wherein said radioluminescent light source and said sensing matrix are spaced apart from each other to define a test cell therebetween.

27. The system of claim 25, wherein said sensing matrix includes a film containing a luminophore and said film is spaced apart from said radioluminescent light source.

28. The system of claim 25, further comprising a probe housing said radioluminescent source, said probe having:

an outer surface coupled to said sensing matrix, said sensing matrix having a sensing surface configured to contact a test medium; and a body configured to transmit light from said radioluminescent source to said sensing matrix, at least a portion of said body being positioned between said sensing matrix and said radioluminescent source.

29. The system of claim 28, wherein said probe includes a mirror to reflect electromagnetic radiation emitted from said radioluminescent light source.

30. The system of claim 29, further comprising an optical fiber coupling said probe to said photodetector, said probe being configured to transmit electromagnetic radiation from said sensing matrix to said photodetector.

31. The system of claim 25, wherein said sensing matrix includes a ruthenium complex configured to detect oxygen.

32. The system of claim 25, wherein said radioactive constituent includes at least one of $^3$H or $^{147}$Pm.

33. The system of claim 25, wherein said phosphor constituent includes at least one of $Y_2O_2S$:Eu, $Y_3(Al,Ga)_5O_{12}$:Ce, or ZnS:Ag.

* * * * *